United States Patent [19]

Barbee et al.

[11] Patent Number: 5,386,121

[45] Date of Patent: Jan. 31, 1995

[54] IN SITU, NON-DESTRUCTIVE CVD SURFACE MONITOR

[75] Inventors: Steven G. Barbee, Dover Plains; Tony F. Heinz, Chappaque; Leping Li, Poughkeepsie; Victor J. Silvestri, Hopewell Junction, all of N.Y.

[73] Assignee: International Business Machines Corporation, Armonk, N.Y.

[21] Appl. No.: 173,314

[22] Filed: Dec. 23, 1993

[51] Int. Cl.6 ............................................. G01N 21/09
[52] U.S. Cl. .................... 250/341.8; 356/246
[58] Field of Search ............... 250/341, 343; 356/244, 356/246, 326, 445

[56] References Cited

U.S. PATENT DOCUMENTS

| | | |
|---|---|---|
| 4,085,326 | 4/1978 | Williams . |
| 4,113,514 | 9/1978 | Pankove et al. . |
| 4,411,989 | 10/1983 | Grow ................................. 435/20 |
| 4,454,472 | 6/1984 | Moore . |
| 4,595,833 | 6/1986 | Sting . |
| 4,631,408 | 12/1986 | Zelmanovic et al. . |
| 4,980,551 | 12/1990 | Wong . |
| 4,980,772 | 6/1979 | Reedy . |
| 5,054,920 | 10/1991 | Doyle ................................. 356/246 |
| 5,066,599 | 11/1991 | Kaneta et al. . |

FOREIGN PATENT DOCUMENTS

| | | | |
|---|---|---|---|
| 57-111423 | 7/1982 | Japan ................. | 250/341 |
| 63-157434 | 6/1988 | Japan . | |
| 02168141 | 6/1990 | Japan . | |

OTHER PUBLICATIONS

J. A. O'Neill, et al.; "Infrared Internal Reflection Studies of the Surface Photochemistry of Dimethylcadmium on Silicon"; J. Vac. Sci. Technol.A7 (3), May/Jun. 1989, pp. 2110–2114.

Y. J. Chabal, et al.; "Hydrogen Chemisorption on Si(111)-(7X7) and -(1X1) Surfaces"; (c) 1983 The American Physical Society, pp. 4472–4479.

Y. J. Chabal, et al.; "Infrared Spectroscopy of Si(111) and Si(100) Surfaces After HF Treatment: Hydrogen Termination and Surface Morphology"; J. Vac. Sci. Technol.A7 (3), May/Jun. 1989, pp. 2104–2109.

Primary Examiner—Paul M. Dzierzynski
Assistant Examiner—Richard Hanig
Attorney, Agent, or Firm—Whitham, Curtis, Whitham & McGinn

[57] ABSTRACT

A non-intrusive, in-situ monitoring technique and apparatus is used for evaluating the presence and extent of a critical contaminating or passivating layer on a transparent sample, prior to a subsequent process step. A multiple internal reflection apparatus and method without the need for aligning mirrors reduces the time to maximize the light intensity through the sample and to the detector and eliminates the intensity loss due to reflection from each mirror. The technique and apparatus can be used to monitor for a critical hydrogen passivation layer so that it is maintained on the silicon surface right up to the point at which the reactants are introduced for the deposition. The in-situ monitoring and process control technique uses Fourier Transform Infrared Spectroscopy with Multiple Internal Reflections (FTIRS-MIR) which looks at the Si—H bond vibration. Apparatus implementing the technique provides a means of insuring reproducibility in films through direct monitoring of the passivating layer. The technique can be utilized in UHV Chemical Vapor Deposition (CVD) Low Pressure CVD (LPCVD), mid-pressure and atmospheric Chemical Vapor Deposition (CVD) systems. The technique provides a powerful experimental technique for correlating imposed experimental conditions with the presence or destruction of the passivation and the subsequent film quality obtained. The method is applicable to any portion of the electromagnetic spectrum for which the sample is transparent and internally reflecting with the absorption of energy at the sample's surface attributable to any species of interest that can be detected.

14 Claims, 10 Drawing Sheets

IN SITU, NON-DESTRUCTIVE CVD SURFACE MONITOR

BACKGROUND OF THE INVENTION

1. Field of the Invention

The present invention relates to a general surface monitoring method which uses samples prepared for multiple internal reflection and subsequent spectroscopy to detect the surface condition of the sample. A particular application of the method is for in-situ monitoring, by Fourier Transform Infrared Spectroscopy using Multiple Internal Reflectance (FTIRS-MIR), of surface contamination or lack of hydrogen passivation on a silicon sample interrupted at any point in the manufacture of semiconductor devices prior to film growth or deposition by physical or chemical means (such as epitaxy).

2. Description of the Prior Art

Fourier Transform Infrared Spectroscopy using Multiple Internal Reflections (FTIRS-MIR) is a well-known technique to improve the signal to noise ratio (S/N) by multiple interactions with the sample surfaces for a given short period of time. This allows a real-time surface monitoring capability at the monolayer level.

Y. J. Chabal, G. S. Higashi and K. Raghavachari in "Infrared spectroscopy of Si(111) and Si(100) surfaces after HF treatment: Hydrogen termination and surface morphology", *Journal of Vacuum Science and Technology*, May/June 1989 (2104–2109), found that upon HF treatment, the surfaces of both Si(111) and Si(100) are microscopically rough with mono-, coupled mono-, di- and trihydride termination. Si(111) surface forms a regular array of double-layer steps with evidences for a dimer reconstruction of the step atoms. The trihydride interacts with the steps in a manner that breaks the degeneracy of the asymmetric strength.

Kaneta et al., U.S. Pat. No. 5,066,599, Silicon Crystal Oxygen Evaluation Method using Fourier Transform Infrared Spectroscopy (FTIR) and Semiconductor Device Fabrication Method using the Same, describe a technique of measuring oxygen impurities in silicon crystals. In this technique several measurements must be taken to calculate the absorption peaks of oxygen impurity in the silicon crystal. For this reason very small vibrational reflections cannot be detected.

Takizawa et al., Japanese laid open application No. 63-157343, Measuring Method for Impurity Concentration of P-type Silicon Crystal, demonstrate another technique for measuring impurities in silicon crystals. In their procedure, an intermediate crystal is sandwiched between two highly doped P-type silicon crystals, and the highly doped P-type silicon crystals are irradiated by an infrared light ray which is reflected between the two crystals through the intermediate crystal. The infrared spectra of the exiting light ray is used as a measure of the impurity in the highly doped P-type silicon crystals.

Sting, U.S. Pat. No. 4,595,833, Multiple Internal Reflection Cell Optical System for use in Infrared Spectrophotometry of Liquid and Fluidized Samples, uses reflaxicon optics for directing infrared radiation from a source into the entry and directs radiation from the exit to a detector. This invention is best used on liquids and fluidized samples. This method is not useful for evaluating impurities in silicon wafers without destroying their structure.

Passivation of silicon surfaces prior to film formation on such surfaces is essential to prevent oxide or carbide formation. The passivation must be maintained from the point of cleaning, through the loading and up to the time the gases for deposition are admitted to the system. There has been variability observed in both the Ultra-High Vacuum (UHV), Low Temperature Epitaxy (LTE), and Medium Temperature Epitaxy (MTE) film growth quality and epitaxial interface contaminants. Oxygen, carbon and fluorine have been observed by Second Ion Mass Spectrometry (SIMS) even though surfaces were passivated with hydrogen via a hydrofluoric acid (HF) final rinse step.

For the MTE case (850° C. films), the HF final rinse step was also shown to be beneficial in reducing oxide and carbon content and corresponding film improvements were observed with these reductions. Variability and reproducibility in both epitaxial processes is troublesome, however.

It has been demonstrated that various surface hydrides are strongly dependent on the hydrogen exposure and the adsorption temperature. In general, the higher hydrides ($SiH_2$ and $SiH_3$) are formed at high hydrogen exposures. A general trend has been observed that the formation of higher hydrides is favored by low adsorption temperature. The apparent sticking coefficient as well as the saturation coverage of hydrogen on $Si(111)$-$7 \times 7$ are temperature dependent, resulting from a series of competing surface reactions with different temperature dependencies. The existence of tilted monohydrides and $SiH_2$ and $SiH_3$ species on the surface show that an extensive breaking of Si—Si bonds must occur during hydrogen adsorption. The bond breaking induces a disordering of the $Si(111)$-$7 \times 7$ surface.

SUMMARY OF THE INVENTION

It is therefore an object of the present invention to provide an apparatus and non-intrusive, in- or ex-sim technique to quickly and easily determine the presence and extent of surface-bonded molecules which may comprise a passivation or contamination or other layer on a sample, which may be necessary or deleterious prior to a subsequent process step such as an epitaxial growth.

According to a preferred embodiment of the invention, there is provided an apparatus which eliminates the need for careful alignment of mirrors, initially and after re-insertion of the sample, in order to maximize the spectroscopic signal. Usually four mirrors are provided with MIR accessories to spectroscopes. A loss of signal strength occurs at each of the four mirrors' reflecting surfaces. This loss is eliminated in the method and apparatus of the invention. Furthermore, a great deal of time can be spent in aligning the four mirrors to maximize the amount of light (signal strength) in the optical path of the apparatus. The method and apparatus of this invention requires only a single quick adjustment. The sample can be removed and replaced without losing alignment.

A specific application of the invention is an in-sire, nondestructive methodology for monitoring whether critical hydrogen passivation can be maintained on the silicon surface right up to the next step, such as the point at which the reactants are introduced for an epitaxial deposition.

The in-situ monitoring and process control technique of the invention uses spectroscopy for surface species identification. Any suitable wavelength may be used in the electromagnetic spectrum, as long as it can pass through the sample and be multiply reflected at the sample's surfaces. A specific example is the use of Fourier Transform Infrared Spectroscopy using Multiple Internal Reflections (FTIRS-MIR) which can look at the Si—H bond vibration on a silicon sample's surfaces. An apparatus implementing the technique according to the invention provides a means of ensuring reproducibility in physically or chemically deposited films through direct monitoring of any surface contaminating or passivating layer prior to film formation. For instance, the invention can be utilized in both UHV and Low Pressure Chemical Vapor Deposition (UHVCVD and LPCVD), mid-pressure, atmospheric Chemical Vapor Deposition (CVD) and Physical Vapor Deposition (PVD) systems. The invention provides a convenient way to correlate process conditions imposed by the presence or destruction of any surface passivation or contamination with the subsequent film quality obtained.

BRIEF DESCRIPTION OF THE DRAWINGS

The foregoing and other objects, aspects and advantages will be better understood from the following detailed description of a preferred embodiment of the invention with reference to the drawings, in which.

DETAILED DESCRIPTION OF A PREFERRED EMBODIMENT OF THE INVENTION

Figure 1:
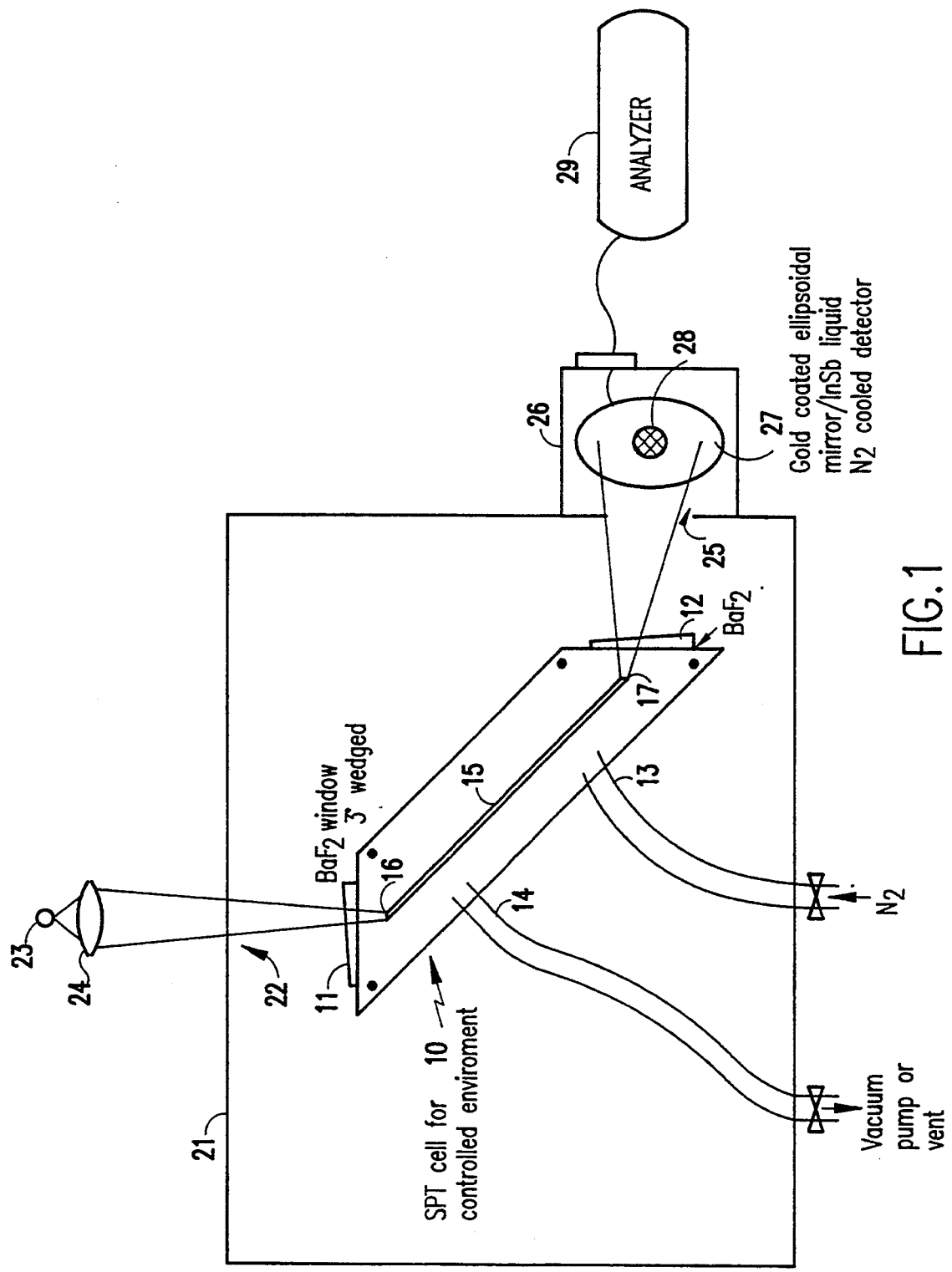
FIG. 1 is a schematic diagram of apparatus for testing which implements the technique according to the invention, where it is noted that no alignment mirrors are required.

Referring now to the drawings, and more particularly to FIG. 1, there is shown an apparatus for testing a silicon wafer. The apparatus comprises an infrared (IR) interferometer (Bomen) and includes a Single Pass Trapezoidal (SPT) cell 10 equipped with an input $BaF_2$ window 11 and an output $BaF_2$ window 12. The two $BaF_2$ windows are wedged at about 3 degrees, such that the opposing surfaces are not parallel which might result in a signal decrease due to interference. The SPT cell 10 additionally has an input port 13 and an output port 14. The input port 13 is connected to receive a gas, and the output port 14 is connected to a vacuum pump (not shown) or is simply vented. The SPT cell 10 can be evacuated below atmospheric pressure or purged with various gases without absorption in the spectral region of interest, such as nitrogen ($N_2$), from a gas source to the input port 13 at any reduced pressure as well as at atmospheric pressure.

A SPT cell 10 is designed to receive a silicon substrate 15 such that the bevelled end of the sample is flush with one end of the adjacent housing. This provides an automatic alignment position for the sample should it be necessary to remove the sample, expose it to a treatment, and replace it, for a before and after comparison. In our example, the substrate has a critical passivating hydrogen layer necessary for successful epitaxial growth, and it is the integrity of this critical passivating layer that is monitored by the invention. As shown in more detail in FIG. 2, the silicon substrate 15 has opposing edges 16 and 17 beveled at 45°, parallel with the opposite trapezoidal faces of the SPT cell 10. These edges 16 and 17 are respectively self-aligned with the input and output windows of the cell 10.

Figure 2:
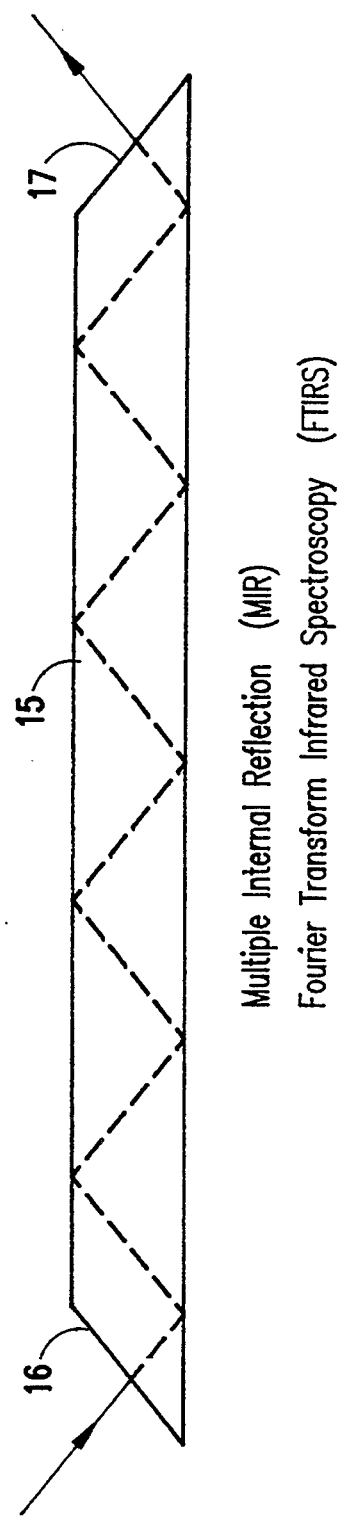
FIG. 2 is a cross-sectional view of a hydrogen passivated silicon wafer showing the multiple internal reflections of the infrared light passing through it in the apparatus shown in FIG. 1.

The SPT cell 10 is mounted within a housing 21 having an opening 22. Light from a modulated light source, such as from a FTIR spectrometer 23, is focussed by lens 24 through input window 11 on the beveled edge 16 of the silicon substrate 15. As shown in FIG. 2, the IR light ray is totally reflected at the interfaces of the silicon substrate and the surrounding medium and propagates to the opposite edge 17 where it exits through the output window 12. Opposite output window 12 is a second opening 25 in the housing 21. A subhousing 26 is attached to the housing 21 and encloses an ellipsoidal mirror 27 and IR detector 28. The ellipsoidal mirror, which may coated with a thin layer of gold, focusses the exited IR light on a liquid nitrogen cooled InSb detector 28 in the 2100 $cm^{-1}$ region (Si—H stretch absorption). The output of the detector 28, which gives the best signal detection sensitivity in the 2100 $cm^{-1}$ region (Si—H stretch absorption), is connected to an analyzer 29 exterior to the subhousing 26.

Test sample silicon substrates employed were 1 mm thick Si(111) and Si(100) with resistivities of approximately 30 ohm-cm. The test samples were 5 cm long and 2 cm wide with 45° bevels at each of the short sides, as generally shown in FIG. 2. The infrared light was passed through input $BaF_2$ window 11 of SPT cell 10 to the beveled edge 16 of silicon wafer sample 15. After multiple internal reflections, the infrared beam was reflected through the output $BaF_2$ window 12 to the InSb detector 28. A vacuum pump was used in conjunction with the chamber 21 to remove the species in the air such as $CO_2$ and $H_2O$ which give rise to undesirable gas phase IR spectrum which could mask and/or interfere with spectrum due to surface species.

Figure 3:
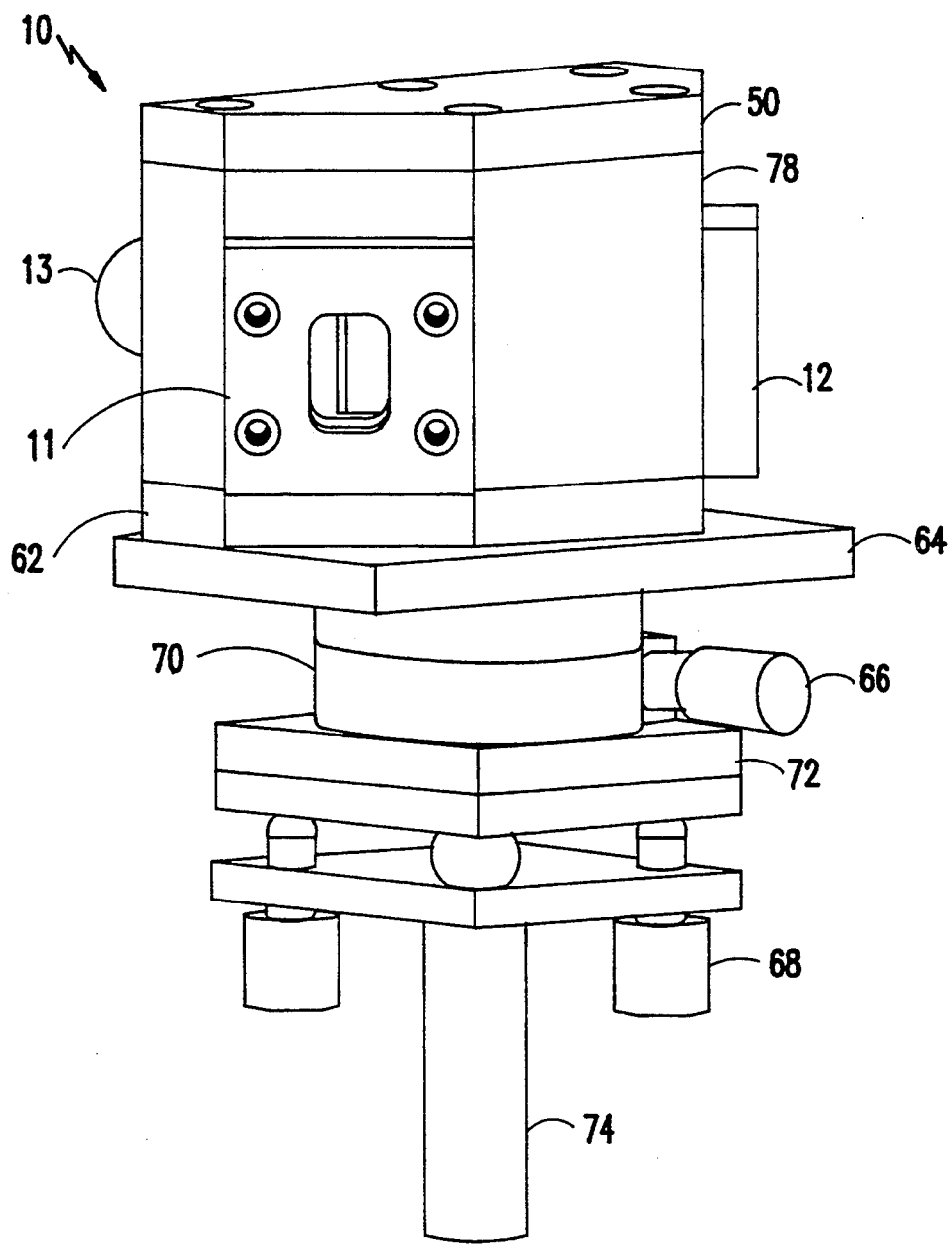
FIGS. 3 and 4 are, respectively, left quarter and right quarter views of the cell assembly with adjustment micrometers or screws for leveling and aligning the sample.
Figure 4:
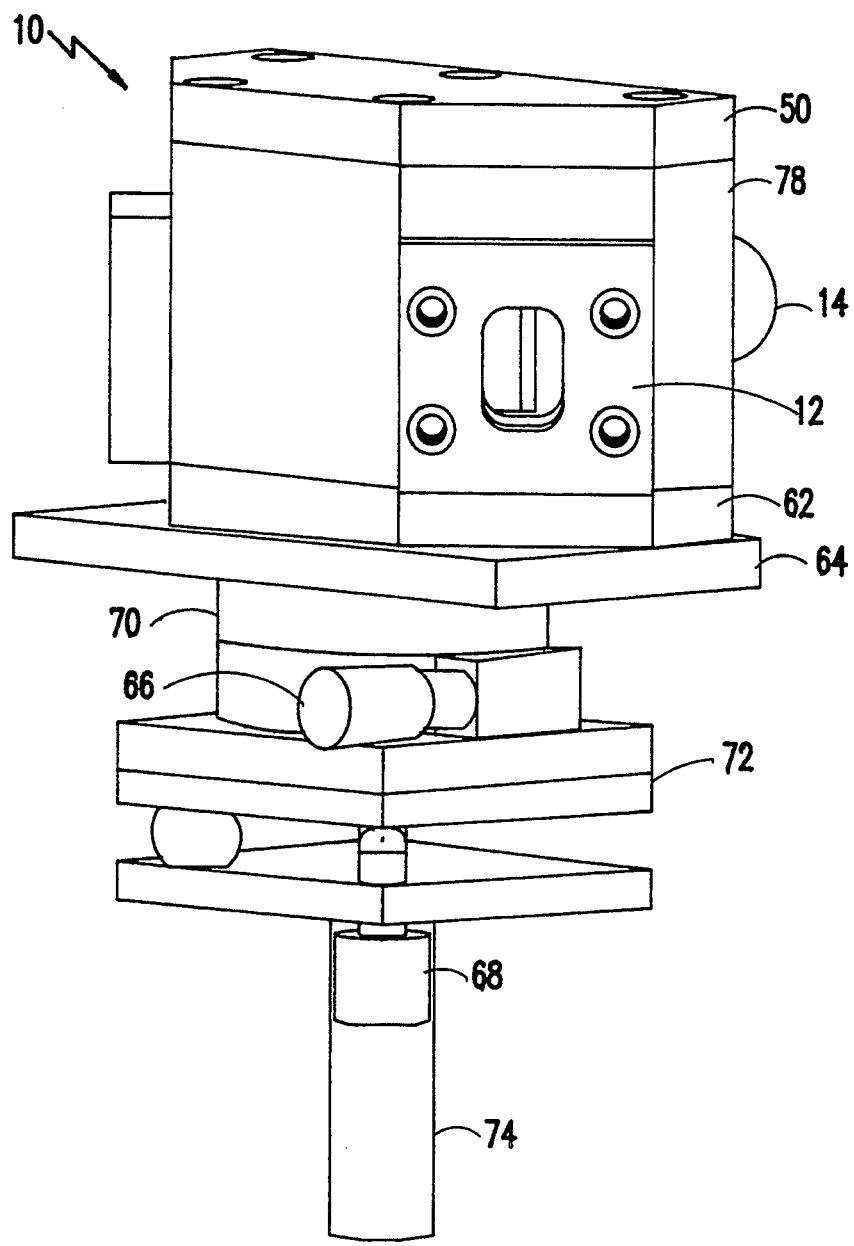

The apparatus is depicted with more detail in FIGS. 3 through 8. Referring first to FIGS. 3 and 4, there are shown left quarter and right quarter views of the cell 10 on a mounting assembly. Parts of the cell which can be seen are the top plate 50 and bottom plate 62, which are bolted to the cell body 78. The input window 12 is best seen in FIG. 4, while the output window 11 is best seen in FIG. 3. The mounting assembly has base mounting plate 64 to which the cell is attached. The base mounting plate 64 is part of a rotating section 70 which allows rotation of the cell, and hence the sample within the cell, for alignment purposes. The rotating section 70 is adjusted using a micrometer 66. The rotating section is supported by a subbase assembly 72 which includes micrometers 68 and 69 for leveling the sample, by adjusting the subbase assembly 72. The entire assembly rests on a rod 74 for mounting in a mounting device, such as a magnetic mount.

The mounting of the cell 10 in the manner shown in FIGS. 3 and 4 allows for secure and repeatable mounting with the micrometers providing optical alignment. Once properly aligned, the sample attached to the top plate 50 can be removed for some ex-situ treatment and returned to the apparatus for post-treatment analysis (such as by subtracting or dividing the pre-treatment spectrum from the post-treatment spectrum); it will retain its previous alignment without need for subsequent re-alignment.

Figure 5:
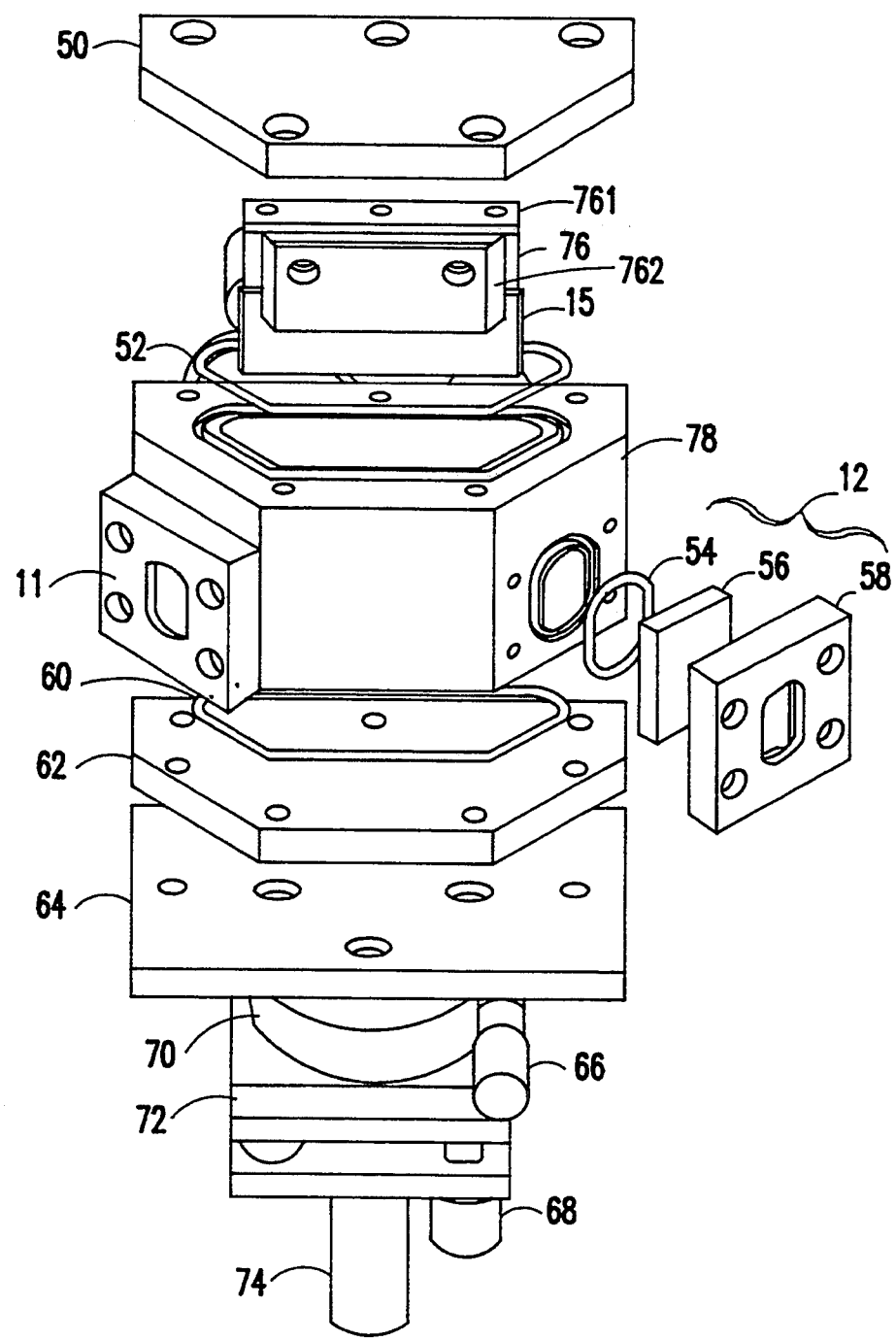
FIGS. 5 to 8 are exploded-view diagrams from different viewing perspectives showing the entire assembly resting on a rod for mounting in a mounting device, such as a magnetic mount.

FIG. 5 is a first exploded view as seen from the front of the cell. The top 50 of the cell is bolted to the cell body 78 with O-ring 52 making the seal. The substrate 15 is held by clamping through spring-loaded fixture 76 which is attached to the interior surface of top plate 50. The fixture 76 comprises a main body 761 attached to the top plate 50 and a removable clamping plate 762 which is attached to the main body 761 by spring-loaded screws or other suitable clamping mechanisms. The substrate 15 may be protected with one or more pads, typically Teflon plastic.

Input window 12 is affixed to the cell with sealing O-ring 54, wedged $BaF_2$ window 56, and window bezel 58. The output window 11 is similarly affixed to the cell. The bottom plate 62 is bolted to the cell body 78, also with a sealing O-ring 60. The micrometer 66 for adjusting alignment and the micrometers 68 for adjusting level are found beneath the mounting plate 64.

Figure 6:
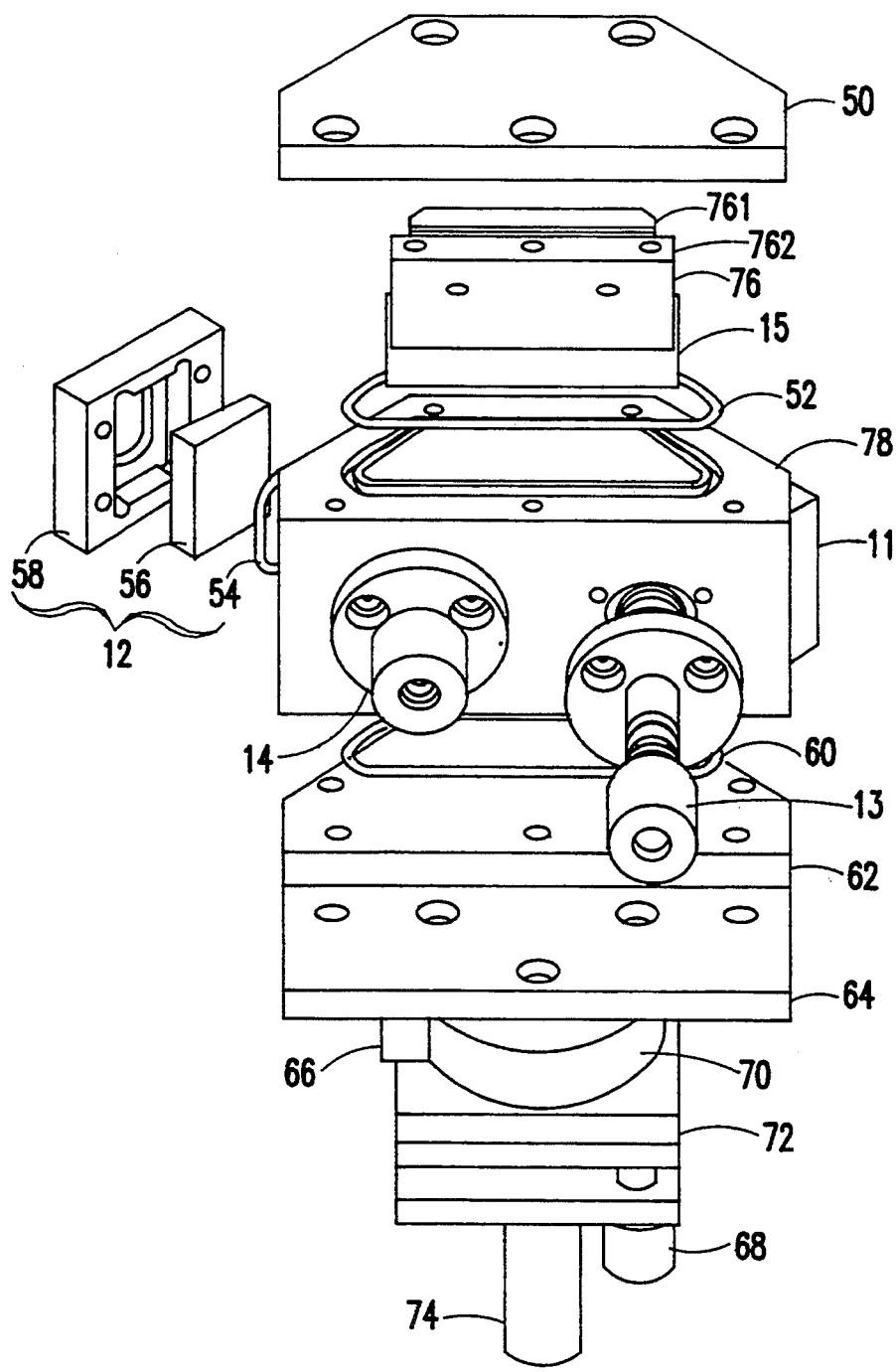
Figure 7:
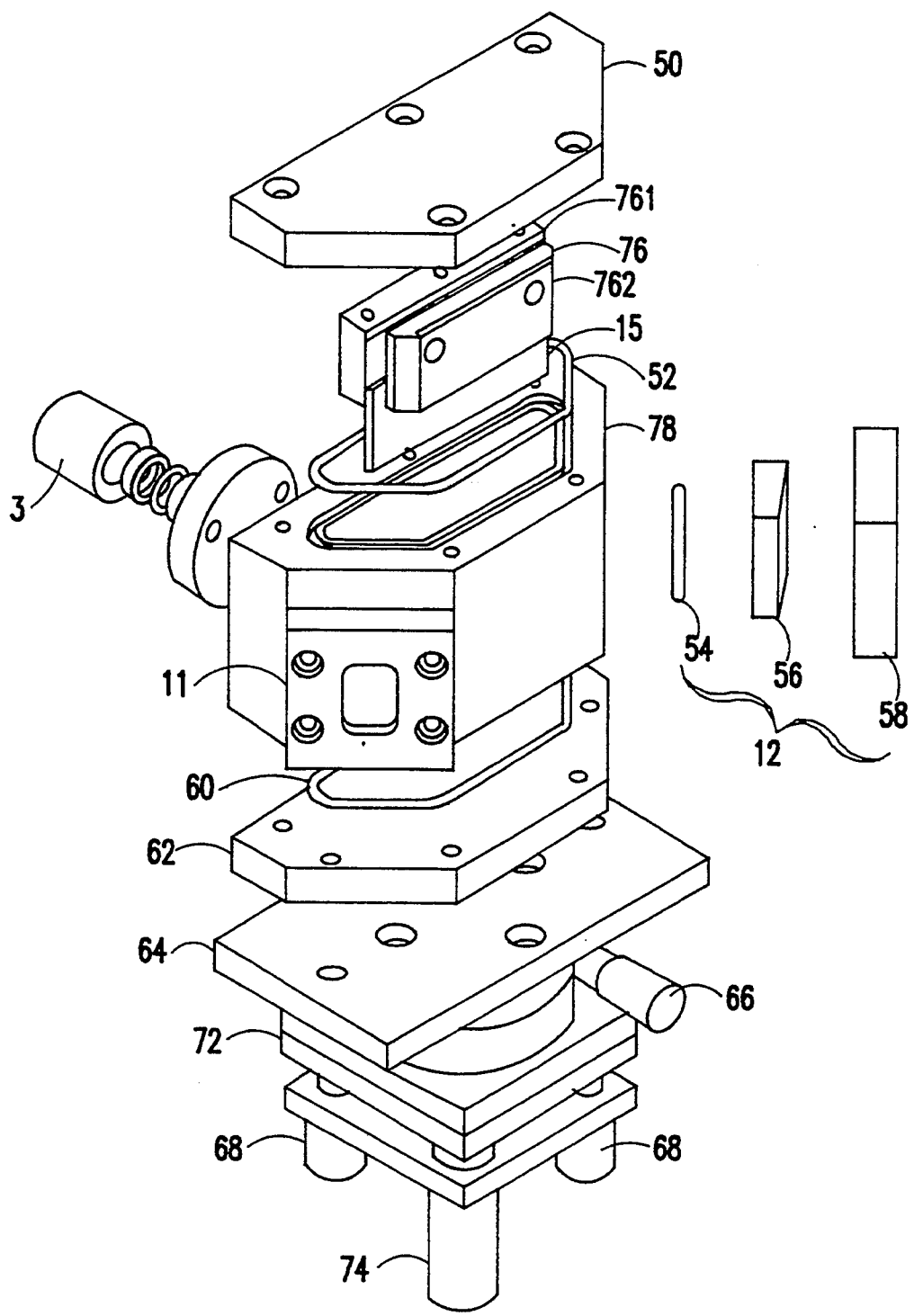
Figure 8:
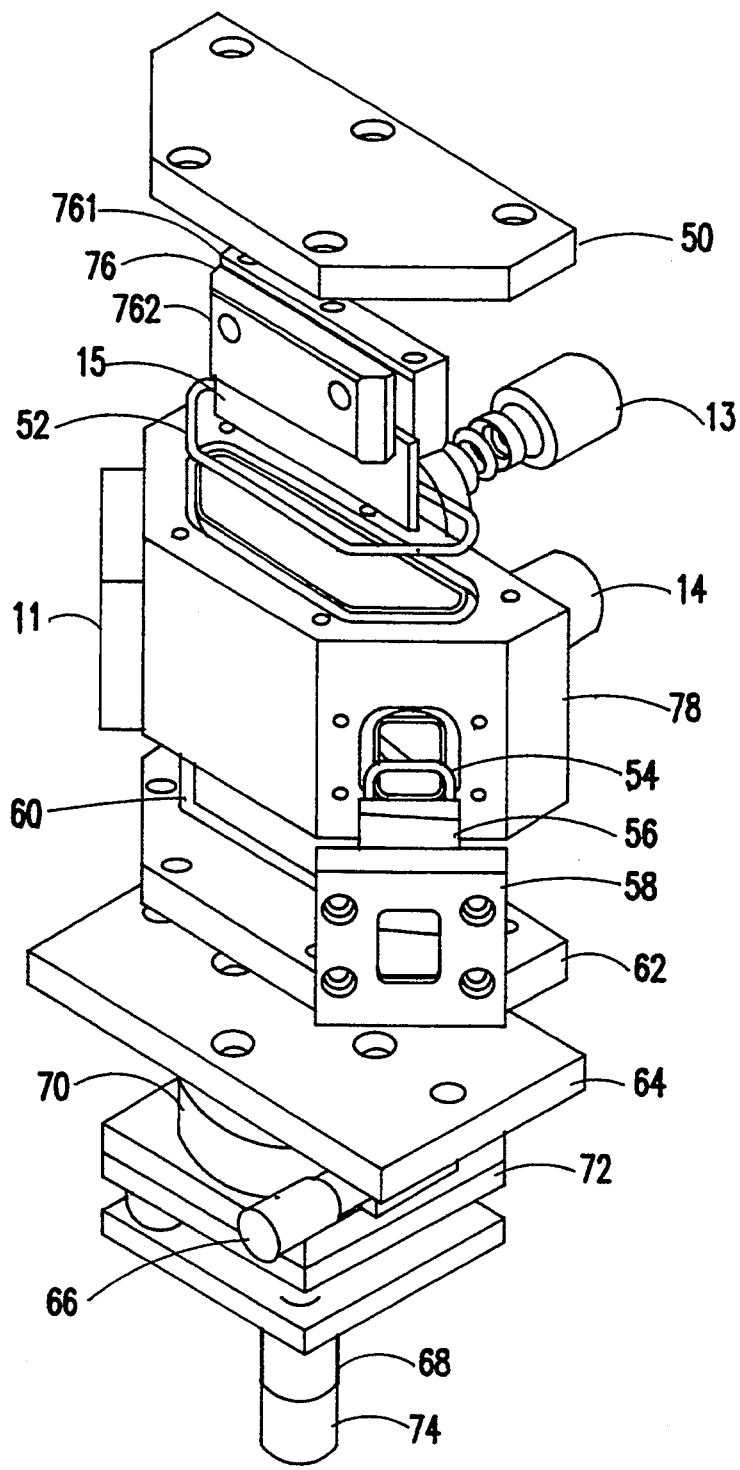

FIG. 6 is an exploded rear view of the cell and mounting assembly. This view shows input port 13 and output port 14. FIG. 7 is an exploded view of a 235° rotation on the Z-axis from the front position. FIG. 8 is a similar exploded view showing a 315° rotation on the Z-axis from the front position.

As shown in FIG. 2, the infrared radiation incident on the input bevel is internally reflected on both surfaces in the manner depicted. For the process, the infrared radiation normally is internally reflected a total of 70 times. This multiple internal reflection geometry makes it possible to detect vibrational absorptions as small as $$\frac{\Delta R}{R} = 10^{-6}$$

per reflection.

The reflected light from the exit beveled edge 17 on the silicon substrate 15 is passed through the output $BaF_2$ window, collected on the gold coated ellipsoidal mirror 27 and focused onto an InSb detector 28.

Figure 9:
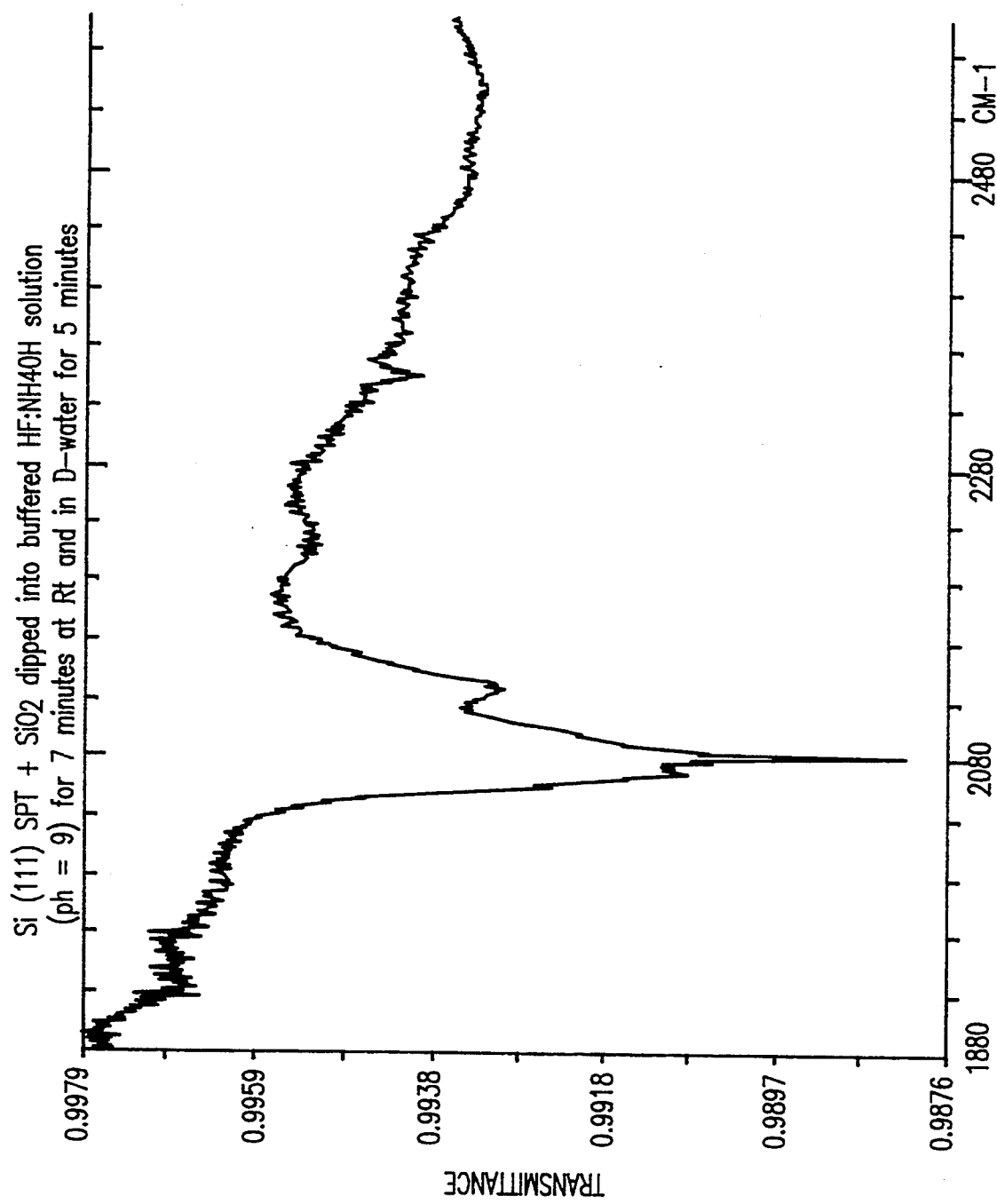
FIG. 9 is a graph showing a recorded infrared spectrum obtained using the apparatus shown in FIG. 1 with hydrogen passivation.

FIG. 9 is a graph showing recorded infrared spectra obtained using the apparatus shown in FIG. 1 with hydrogen passivation. Following passivation of the surfaces using liquid HF without an $H_2O$ rinse, the silicon substrate 15 is mounted in the cell 10 and infrared spectra are recorded using analyzer 29. With hydrogen passivation present on the surface of the silicon, the spectrum shows a characteristic peak for the Si—H vibration at approximately 2083 $cm^{-1}$, as shown in FIG. 9. With the reduced passivation due to gasous species reacting on the passivating surfaces, the sharp peak at 2083 $cm^{-1}$ is dramatically reduced.

Figure 10:
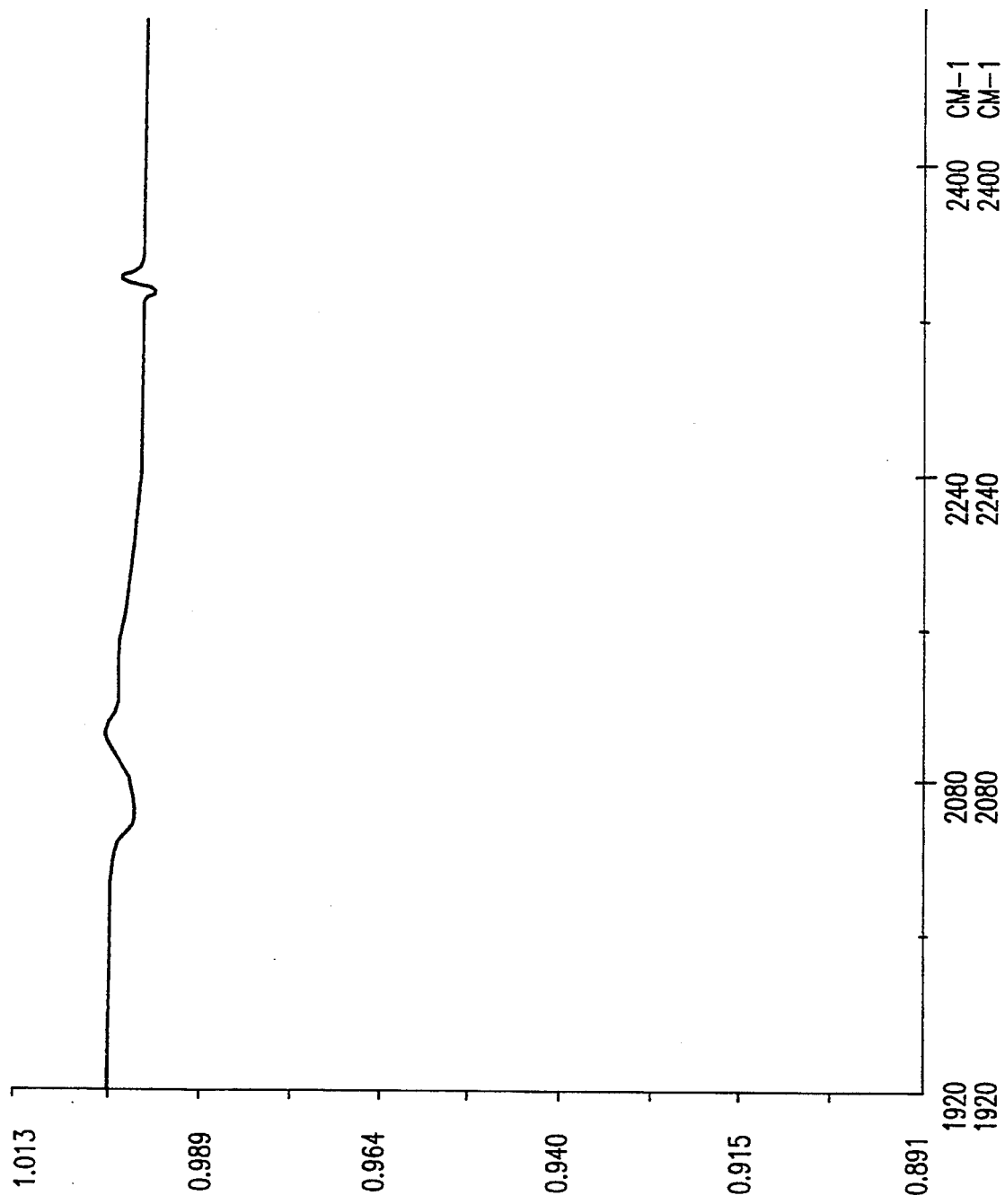
FIG. 10 is a graph showing recorded infrared spectra obtained using the apparatus shown in FIG. 1 with reduced hydrogen passivation due to the surface reaction by reactive species.

In experiments where nitrogen was used to purge the cell containing Si(111) wafer (previously etched with HF), a characteristic trace as shown in FIG. 9 was obtained indicating that passivation was present. With a pump down of the cell, the peak was dramatically reduced resulting in a trace as shown in FIG. 10. For this experiment, it is believed that reactive hydrocarbon radicals and the prolonged mean free path (therefore the long lifetime of the reactive species) introduced with pumping were responsible for the rapid destruction of the hydrogen passivation observed. The traces clearly demonstrate that the in-situ monitoring technique described can readily detect surface changes when destructive species are introduced to the surfaces.

In LTE systems, it has been assumed that hydrocarbons should not be a problem since clean pumping techniques are employed; however, the variability in films observed suggest there may be other factors which lead to the destruction of the passivating hydrogen. This technique would still be useful for LTE in detecting these destructive occurrences. In higher pressure and atmospheric systems, this in-situ monitoring technique can be used for process control essentially giving an operator a "GO" or "NO GO" decision on the epitaxial deposition process.

Maintaining the hydrogen passivation is just as critical in MTE and High Temperature Epitaxy (THE). It has been found, for example, in the MTE case that film quality will deteriorate at observed oxygen levels above 1E18 atoms per $cm^2$ (with SIMS) at the interface. This is believed to be tied to the degree of passivation achieved and maintained prior to first deposition. Carbon levels track similarly and are deleterious to films above specific levels. For the oxygen observations, levels below 1E18 atom per $cm^2$ show good film quality at temperatures where good epitaxy was not thought possible in a ten torr system at an MTE temperature of 850° C.

As discussed previously, nitrogen ambient above the silicon surface after cleaning and throughout the introduction process into an epitaxial system allows the passivating layer to be retained. This purging is applicable to many processes in state-of-the-art deposition systems; therefore, this monitoring technique can be extended to many CVD and PVD process tools by means of SMIF (Standard Mechanical Interface) attachments. It is believed that nitrogen purging can function just as well as a vacuum load lock on most tools, and this is a far less complicated approach. Purging and monitoring appear to be useful even with a secondary vacuum load lock for LTE systems.

This same in-situ technique can also be utilized for monitoring individual gas purity in the gas lines supplying CVD and PVD systems for detecting when contaminants destructive to the passivating layer are present. For this type of monitoring, a passivated silicon substrate would be exposed to the gas in the line. The detector would then evaluate the effect of the gas on the passivating film.

From the experiments, it is reasonably clear that reactive hydrocarbon species are among the destructive contaminants, and elimination of these are desirable in LTE at 600° C., MTE at 850° C., and HTE above 1000° C. epitaxy. The in-situ monitoring technique according to the invention permits an indication ahead of time whether a good epitaxial layer will be achieved. In summary, the new in-situ monitoring technique can be used in gas line monitoring for detecting contaminants which can destroy the passivating layer needed for good epitaxial deposition, as well as the film purity.

While the invention has been described in terms of a single preferred embodiment, those skilled in the art will recognize that the invention can be practiced with modification within the spirit and scope of the appended claims. For example, the light source can be a source having any wavelength so long as it can be modulated, detected and demodulated, and processed by Fourier Transform Spectroscopy. The sample may also be any material so long as it is substantially transparent to the desired wavelength.

Having thus described our invention, what we claim as new and desire to secure by Letters Patent is as follows:

1. An apparatus for monitoring the presence and extent of surface species on an introduced sample, the apparatus comprising:

a single pass trapezoidal cell equipped with an input window and an output window, the cell further being equipped with an input port and an output port, the cell still further being adapted for receiving a substrate the surface of which is to be spectroscopically analyzed for the presence and extent of chemical species, being of a shape suitable for multiple internal reflections, and the opposing edges of which can be aligned to face the said input and output windows of the cell;

a gas source connected to the input port of said cell, and a vacuum source connected to the output port of said cell to allow the measurement to be made in an inert, non-radiation absorbing environment, or an intentionally reactive environment;

a light source chosen such that the substrate and windows are transparent to it, positioned for providing light to the input window of said cell, the light passing through the input window for entering a first bevelled edge of the substrate, the light thereafter being internally reflected within the substrate and exiting at a second opposing bevelled edge of the substrate, the light thereupon being exited through the output window;

a detector receiving light exited through the output window and generating a signal proportional to detected light; and an analyzer analyzing the signal proportional to detected light and providing an indication of the presence of chemical species present upon the substrate.

2. The apparatus of claim 1 wherein said input window and said output window are $BaF_2$, the two $BaF_2$ windows being wedged at around 3° to remove interference.

3. The apparatus of claim 2 wherein the substrate analyzed is silicon bevelled at 45 degrees.

4. The apparatus of claim 2 further comprising an ellipsoidal mirror for collecting and focussing the exited light and wherein said detector is a liquid $N_2$ cooled detector in the 2100 $cm^{-1}$ region for detecting the collected and focused exited light from said ellipsoidal mirror.

5. The apparatus of claim 1 wherein the cell comprises:

a hollow trapezoidal body having said input and output windows and said input and output ports and at least one opening to an interior of said hollow trapezoidal body;

a cover plate sealingly closing said at least one opening to the interior of the hollow trapezoidal body;

a clamping fixture affixed to said cover plate and projecting within the interior of the hollow trapezoidal body, said clamping fixture being adapted to hold said substrate.

6. The apparatus of claim 5 wherein said input window and said output window are $BaF_2$, the two $BaF_2$ windows being wedged at around 3° to remove interference due to reflected and transmitted input light beams at window surfaces.

7. The apparatus of claim 6 wherein the substrate analyzed is silicon bevelled at 45 degrees.

8. The apparatus of claim 6 further comprising an ellipsoidal mirror for collecting and focussing the exited light and wherein said detector is a liquid $N_2$ cooled detector in the 2100 $cm^{-1}$ region for detecting the collected and focussed exited light from said ellipsoidal mirror.

9. The apparatus of claim 5 wherein said clamping fixture comprises first and second opposing clamping pieces, said first clamping piece being affixed to an interior surface of said cover plate and said second clamping piece being attached to said first clamping piece, said clamping pieces being provided with one or more pads for rigidly holding the substrate using compression.

10. The apparatus of claim 5 wherein the entire cell is positioned securely and repeatably upon a mounting mechanism, said mounting mechanism comprising:

a micrometer-adjusted rotating section for aligning the cell and a substrate within said cell; and one or more micrometer screws to allow leveling of the cell, said adjusting micrometers providing optical alignment, the cell containing a substrate, once properly aligned, the substrate attached to the cover plate can be removed for ex-situ treatment and returned to the cell assembly for a post-treatment analysis while retaining a previous alignment of the cell and the substrate with no need for subsequent re-alignment.

11. A method for monitoring the presence of a critical passivating hydrogen layer on a silicon substrate prior to epitaxial deposition, the method comprising the steps of:

providing a single pass cell equipped with an input window and an output window, the cell further being equipped with an input port and an output port, the cell still further being adapted for receiving a silicon substrate;

providing a silicon substrate having a hydrogen passivation layer present on the surface thereof, the sample substrate having opposing edges to be aligned with said input and output windows and being of a shape suitable for multiple internal reflections;

supplying a gas, without absorption in the spectral region of interest, from a gas source to the input port of said cell, and drawing a vacuum from a vacuum source to the output port of said cell;

illuminating the input window of said cell with a modulated infrared light, the infrared light passing through the input window for entering a first edge of the silicon substrate, the light thereafter being internally reflected within the substrate and exiting at a second opposing edge of the substrate, the light thereupon being exited through the output window;

detecting and analyzing the exited light as gas from said gas source is input into said cell and exited through the output port of said cell by said vacuum source and providing an indication of the presence and extent of a hydrogen passivation layer and other surface species upon the sample silicon substrate.

12. The method recited in claim 11 further comprising the steps of collecting and focussing the exited light using an ellipsoidal mirror and wherein the step of detecting is performed using a liquid $N_2$ cooled detector in the 2100 $cm^{-1}$ region.

13. A method for detecting changes in chemical species on a substrate's surfaces, in the absence of a passivating or contaminating layer, the method comprising the steps of:

providing a single pass cell equipped with an input window and an output window, the cell further being equipped with an input port and an output port, the cell still further being adapted for receiving a substrate;

providing a substrate with opposing edges to be aligned with said input and output windows and being of a shape suitable for multiple internal reflections;

supplying a gas, without absorption in the spectral region of interest, from a gas source to the input port of said cell, and drawing a vacuum from a vacuum source to the output port of said cell;

illuminating the input window of said cell with a modulated light source, the light passing through the input window for entering a first edge of the substrate, the light thereafter being internally reflected within the substrate and exiting at a second opposing edge of the substrate, the light thereupon being exited through the output window;

detecting and analyzing the exited light as gas from said gas source is input into said cell and exited through the output port of said cell by said vacuum source and providing an indication of changes in species type and extent on the surface of the substrate.

14. The method recited in claim 13 further comprising the steps of collecting and focussing the exited light using an ellipsoidal mirror and wherein the step of detecting is performed using a liquid $N_2$ cooled detector in the 2100 $cm^{-1}$ region.

* * * * *